United States Patent [19]

Albright et al.

[11] 4,260,816

[45] Apr. 7, 1981

[54] NAPHTHYLOXYALKYLAMINOBENZOIC ACIDS, SALTS AND ESTERS THEREOF

[75] Inventors: Jay D. Albright, Nanuet; Thomas G. Miner, Chester; Robert G. Shepherd, South Nyack, all of N.Y.

[73] Assignee: American Cyanamid Company, Stamford, Conn.

[21] Appl. No.: 59,915

[22] Filed: Jul. 20, 1979

Related U.S. Application Data

[63] Continuation-in-part of Ser. No. 891,655, Mar. 30, 1978, abandoned, which is a continuation of Ser. No. 760,600, Jan. 19, 1977, abandoned, which is a continuation-in-part of Ser. No. 639,018, Dec. 9, 1975, abandoned.

[51] Int. Cl.$^3$ .................. C07C 101/60; C07C 101/58
[52] U.S. Cl. ...................................... 562/452; 562/427; 562/455; 560/45; 560/10; 260/465 D; 424/304; 424/309; 424/319; 546/330; 546/335

[58] Field of Search ............... 562/433, 455, 452, 430, 562/427; 560/45, 59, 10; 200/465 D; 546/330, 335

[56] References Cited

U.S. PATENT DOCUMENTS

| | | | |
|---|---|---|---|
| 2,946,790 | 7/1960 | Renz et al. | 260/473 R |
| 3,551,478 | 12/1970 | Schmitt et al. | 560/45 |
| 3,985,790 | 10/1976 | Metz et al. | 560/45 |
| 4,073,935 | 2/1978 | Grile et al. | 560/45 |

*Primary Examiner*—Natalie Trousof
*Assistant Examiner*—James H. Reamer
*Attorney, Agent, or Firm*—Jack W. Richards, Jr.

[57] ABSTRACT

This disclosure describes pharmaceutical compositions having hypolipidemic and/or hypoglycemic activity which contain a substituted naphthyloxyalkylaminobenzoic acid or salt or ester thereof.

10 Claims, No Drawings

NAPHTHYLOXYALKYLAMINOBENZOIC ACIDS, SALTS AND ESTERS THEREOF

CROSS REFERENCE TO RELATED APPLICATIONS

This application is a continuation-in-part of our copending application Ser. No. 891,655, filed Mar. 30, 1978, now abandoned, which is a continuation of our application Ser. No. 760,600, filed Jan. 19, 1977, now abandoned, which is a continuation-in-part of our application Ser. No. 639,018, filed Dec. 9, 1975, now abandoned.

DESCRIPTION OF THE INVENTION

This invention relates to compounds which have hypolipidemic activity, to a method for their preparation, and to pharmaceutical compositions comprising them. Many of the compounds of this invention in addition have hypoglycemic activity.

It has been observed that persons with vascular disease are often diabetic or pre-diabetic so it would be therapeutically beneficial if a drug administered to reduce serum-lipid levels also acted to eliminate the hypoglycemic state. In diabetes mellitus, many persons also have elevated levels of lipid (cholesterol, phospholipid and especially triglyceride) in the blood. It is likewise therapeutically beneficial if an antidiabetic hypoglycemic drug which reduces blood-sugar levels also possesses lipid-lowering activity. The most important form of diabetes is the type in which the body tissues are relatively insensitive to the action of insulin. The compounds of the present invention overcome this defect by making the tissues more normally responsive to the biological effects of insulin. Such substances can combat the hyperglycemia and normalize glucose tolerance in insulin-resistant diabetes and thus prevent the disastrous vascular, neurological and renal sequelae of the disease. These compounds reduce glucose levels in hyperglycemic but not in normoglycemic animals. The antidiabetic compounds of the present invention overcome the reduced sensitivity of body tissues to insulin and are therefore useful in treating the most important form of diabetes.

The novel hypolipidemic compounds of the present invention may be represented by the following structural formula:

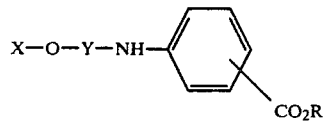

wherein Y is a branched or straight alkylene chain $C_nH_{2n}$ wherein n is 2 to 12; R is selected from the group consisting of hydrogen, lower alkyl, phenyl, p-chlorophenyl, benzyl, lower alkoxyethyl, 3-(lower alkoxy)-2-hydroxypropyl, 2,3-dihydroxypropyl, 3-(lower alkanoyl)oxy-2-hydroxypropyl, and pyridylmethyl; and X is selected from the group consisting of 1-naphthyl, 2-naphthyl, 1,2,3,4-tetrahydro-5-naphthyl, 1,2,3,4-tetrahydro-6-naphthyl and substituted naphthyl such as 4-chloro-1-naphthyl, 4-cyano-1-naphthyl, 4-carboxamido-1-naphthyl, 4-carboxy-1-naphthyl, 4-acetyl-1-naphthyl, 4-fluoro-1-naphthyl, 7-fluoro-1-naphthyl, 5-methoxy-1-naphthyl, 6-methoxy-1-naphthyl, 4-formyl-1-naphthyl, 5-acetamido-1-naphthyl, 5-methanesulfonamido-1-naphthyl, 5-sulfamyl-1-naphthyl, 1-chloro-2-naphthyl, 5-chloro-2-naphthyl, 6-chloro-2-naphthyl and 1-formyl-2-naphthyl; and when R is hydrogen, the pharmaceutically acceptable alkali metal or organic base salts thereof. Suitable lower alkyl groups contemplated by this invention are those having from 1 to 6 carbon atoms, as for example, methyl, ethyl, isopropyl, n-propyl, tert-amyl, n-hexyl and tert-butyl. Suitable $C_nH_{2n}$ alkylene chains are both branched and straight-chain wherein a branch is a lower alkyl group of from 1 to 6 carbon atoms. The novel hypoglycemic compounds of the present invention may be represented by the above structural formula wherein Y is limited to —CH$_2$CH$_2$— and —CH(CH$_3$)CH$_2$—.

This invention is also concerned with the method of treating diabetes and hyperglycemia as well as a method of lowering the sterol and triglyceride level of the serum of warm-blooded animals, employing pharmaceutical dosage forms of the compounds of the formula:

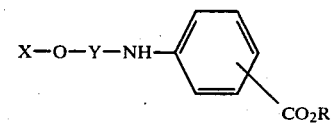

wherein X, Y and R are as previously defined, as well as the pharmaceutically acceptable acid-addition salts and, where R is hydrogen, the alkali metal or organic base carboxylic acid salts thereof.

The novel compounds of the present invention are colorless or tan crystalline solids or colorless or tan oils. The compounds are in general soluble in organic solvents such as benzene, chloroform, dichloromethane, N,N-dimethylformamide, dimethyl sulfoxide and lower alkanols.

The novel compounds of the present invention also are bases and may be converted to their non-toxic addition salts with acids such as sulfuric, hydrochloric, phosphoric, succinic, citric, and the like. The compounds wherein R is hydrogen may be reacted with bases such as sodium hydroxide, potassium hydroxide, and the like or with organic bases such as ethanolamine, triethanolamine, and the like to obtain the corresponding carboxylic acid salts.

The novel compounds are prepared by reacting lower alkyl p-aminobenzoates, p-aminobenzoic acid or other esters of p-aminobenzoic acid with alkylating agents such as naphthyloxyalkyl halides, naphthyloxyalkanol O-sulfates, O-tosylates, O-trifluoromethanesulfonates, or O-methanesulfonates with or without a solvent at 50° to 150° C. for 1-25 hours. Ortho or meta amino compounds are prepared by similar reactions.

Suitable solvents for the alkylations are hexamethylphosphoramide, N,N-dimethylformamide, N,N-dimethylacetamide, lower alkanols, chloroform, dimethyl sulfoxide, benzene, xylene, acetonitrile and the like.

The alkylation reactions may be carried out with an equivalent of base such as an alkali carbonate or bicarbonate. Alternatively, the p-(naphthyloxyalkyl)aminobenzoates may be prepared by reaction of lower alkyl p-aminobenzoates with a naphthyloxyalkyl halide in the presence of an equivalent of sodium hydride in inert solvents such as hexamethylphosphoramide, N,N- dimethylformamide, N,N-dimethylacetamide, xylene and the like at 50° to 170° C. for 1–25 hours.

In the case of naphthyloxyalkylchlorides, the alkylations of lower alkyl p-aminobenzoates may be carried out with an equivalent of sodium or potassium iodide in inert solvents such as hexamethylphosphoramide, N,N-dimethylformamide, N,N-dimethylacetamide and the like.

The p-(naphthyloxyalkyl)aminobenzoic acids of this invention are prepared by hydrolysis of the corresponding esters by reacting with alkali metal hydroxides such as sodium hydroxide or potassium hydroxide in a lower alkanol, water, or an aqueous lower alkanol at 25° to 100° C. Alternatively, the p-(naphthyloxyalkyl)aminobenzoic acids may be prepared by hydrolysis of the p-(naphthyloxyalkyl)aminobenzoates with mineral acids such as hydrochloric, hydrobromic or sulfuric in water or aqueous alkanols.

Esters of p-(naphthyloxyalkyl)aminobenzoic acids may be prepared by conversion of the appropriate acids to an acid chloride with reagents such as thionyl chloride and oxalyl chloride and reacting the intermediate acid chlorides with lower alkanols, di(lower alkyl)aminoethanols, lower alkoxyethanols and the like. Alternatively, the metal (sodium, potassium, zinc and the like) carboxylic acid salts may be reacted with lower alkyl halides, and substituted propyl halides such as 3-halo-1,2-propanediol and the like in solvents such as hexamethylphosphoramide or N,N-dimethylformamide, to give esters of p-(naphthyloxyalkyl)aminobenzoic acids.

The novel p-(naphthyloxyalkyl)aminobenzoates of the present invention may be prepared by reductive alkylation of a lower alkyl p-aminobenzoate or p-aminobenzoic acid with a suitable naphthyloxyalkylaldehyde or ketone in the presence of nobel metal and (or) nickel or cobalt catalyst or a suitable metal hydride. For example, Raney nickel, hydrogen and a naphthyloxyalkylaldehyde may be used to reductively alkylate ethyl p-aminobenzoate. Auxiliary catalysts such as aluminum chloride, piperidine acetate, or acids may be used in the reductive alkylation.

Some of the alkylating agents for the preparation of the novel compounds of this invention may be prepared in the following manner: where W=halogen; n=0, 1–11; R is hydrogen or lower alkyl; $R_1$ and $R_2$ are hydrogen or lower alkyl.

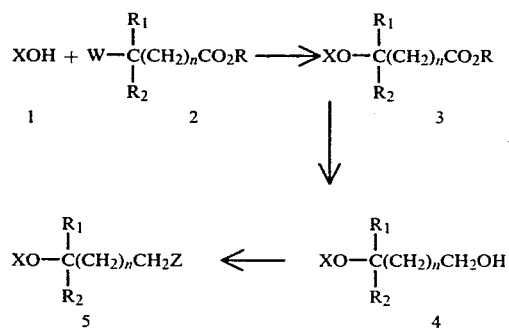

Reduction of the intermediate naphthyloxyalkyl derivatives 3 gives the corresponding alcohols 4 which are converted to the desired alkylating reagents 5 (where Z is halogen, O-methanesulfonate and the like).

The N-acetyl derivatives are prepared by acetylation with acetyl chloride and pyridine or with acetic anhydride. N-Trifluoroacetyl-p-{[2-(1-naphthyloxy)ethyl]amino}benzoic acid results from acylation with trifluoroacetic anhydride and triethylamine. N-Alkyl derivatives may be prepared by reduction of N-acyl benzoate esters with diborane or by alkylation of naphthyloxyalkylaminobenzoate esters. The N-ethyl derivative is also obtained from sodium borohydride, acetic acid and p-{[2-(1-naphthyloxy)ethyl]amino}benzoic acid.

The compounds of the present invention show hypolipidemic activity as determined by animal experiments as follows: The compounds were administered orally admixed with the diet to groups of 4 to 6 male rats, CFE strain from Carworth Farms. A control group of 6 to 8 rats was maintained on the diet alone; test groups were maintained on the diet plus the indicated percentage of compound by weight. After 6-days, treatment serum-sterol concentrations were determined by the extraction method of H. H. Leffler, Amer. J. Clin. Path. 31, 310 (1959), the overall method appropriately modified for use with an automatic mechanical analyzer and the colorimetric determination of Zlatkis et al., J. Lab. Clin. Med. 44, 486 (1953). Serum triglycerides were estimated by the automated procedure of Kessler and Lederer ["Automation in Analytical Chemistry", Skeggs, L. T., (Ed.), Mediad, Inc., New York, 1965, p. 341]. In these tests a compound is considered to have hypolipidemic activity if it depresses serum-sterol levels below that of the controls, and/or depresses triglyceride levels below controls. Table I shows several of the compounds of the present invention and the degree to which they depress serum-sterol and triglyceride levels after a one-week dosing period.

TABLE I

| Compound | % Compound In Diet | % Lowering of Serum Levels | |
|---|---|---|---|
| | | Sterol | Triglyceride |
| p-{[2-(2-Naphthyloxy)ethyl]amino}benzoic Acid | 0.1 | 13 | 47 |
| Ethyl p-{[2-(2-naphthyloxy)ethyl]amino}-benzoate | 0.1 | 10 | 43 |
| p-{[2-(1-Naphthyloxy)ethyl]amino}benzoic Acid | 0.1 | 17 | 42 |
| p-{[2-(4-Chloro-1-naphthyloxy)propyl]-amino}benzoic acid | 0.1 | 18 | 20 |
| Ethyl p-{[2-(1-naphthyloxy)propyl]amino}benzoate | 0.1 | 16 | 45 |
| p-{[2-(1-Naphthyloxy)propyl]amino}benzoic acid | 0.1 | 8 | 43 |
| p-{[3-(1-Naphthyloxy)propyl]amino}-benzoic acid | 0.1 | 19 | 21 |
| Ethyl p-{[3-(1-Naphthyloxy)propyl]-amino}benzoate | 0.1 | 0 | 24 |
| p-{[2-(4-Acetyl-1-naphthyloxy)ethyl]-amino}benzoic acid | 0.1 | 13 | 44 |
| p-{[2-(4-Cyano-1-naphthyloxy)ethyl]-amino}benzoic acid | 0.1 | 0 | 29 |

The antidiabetic insulin-potentiation and hypoglycemic effects of these compounds are demonstrated as shown in Examples 12 and 13.

The compounds of the present invention are useful as hypolipidemic agents in mammals when administered in amounts ranging from about 0.5 mg. per kg. to about 40 mg. per kg. of body weight per day. A preferred dosage regimen for optimum results would be from about 2 mg. per kg. to about 29 mg. per kg. of body weight per day. Thus the daily dosage employed for a subject of about 70 kg. is about 35 mg. to about 2.8 g. and preferably about 140 mg. to about 2.0 g. They are useful as antidiabetic agents in mammals at doses ranging from 5 mg. per kg. to about 200 mg. per kg. of body weight per day.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration the active compounds of this invention may be incorporated with excipients and used in the form of tablets, troches, capsules, elixirs, suspensions, syrups, wafers, chewing gum or the like. Such compositions and preparations should contain at least 0.1% of active compound. The percentage in the compositions and preparations may, of course, be varied and may conveniently be between about 5% and 75% or more of the weight of the unit. The amount of active compound in such therapeutically useful compositions or preparations is such that a suitable dosage will be obtained. Preferred compositions or preparations are prepared so that an oral dosage unit form contains between about 10 mg. and 500 mg. of active compound.

The tablets, troches, pills, capsules and the like may also contain the following: a binder such as gum tragacanth, acacia, corn starch or gelatin; an excipient such as dicalcium phosphate; a disintegrating agent such as corn strach, potato starch, alginic acid and the like; a lubricant such as magnesium stearate; and a sweetening agent such as sucrose, lactose or saccharin may be added or a flavoring. When the dosage unit form is a capsule, it may contain in addition to materials of the above type a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Any material used in preparing any dosage unit form should be pharmaceutically pure and substantially non-toxic in the amounts employed.

In addition, the active ingredients may be incorporated into sustained-release preparations.

SPECIFIC DISCLOSURE

EXAMPLE 1

6-(2-Naphthyloxy)-1-hexanol

To a chilled round bottom blask is added 4.2 g. of 57% sodium hydride in oil, 50 ml. of hexamethylphosphoramide and 15.8 g. of 2-naphthol. After ½ hour the mixture is allowed to warm to room temperature and 13.6 g. of 6-chlorohexan-1-ol is added. The mixture is heated at 110° C. overnight, cooled, diluted with water and extracted with ether. The ether extract is washed with sodium hydroxide solution, then with water, dried (magnesium sulfate) and the solvent removed under vacuum. The solid is dissolved in ether and the solution washed with sodium hydroxide solution. The ether layer is dried (magnesium sulfate) and the solvent removed under vacuum to give 15.9 g. of product, as crystals, m.p. 53°–56° C.

EXAMPLE 2

6-(2-Naphthyloxy)-1-hexanol O-methanesulfonate

To a mixture of 10.4 g. of 6-(2-naphthyloxy)-1-hexanol and 8.1 g. of triethylamine in 250 ml. of dichloromethane chilled to −8° C. under nitrogen is added dropwise 5.1 g. of methanesulfonyl chloride. After one hour at 0° to −6° C., the mixture is washed with cold water, 10% hydrochloric acid solution, saturated sodium bicarbonate solution, saturated sodium chloride solution, and dried (magnesium sulfate). The solvent is removed under vacuum to give the product as a white solid.

EXAMPLE 3

Ethyl p-{[6-(2-naphthyloxy)hexyl]amino}benzoate

A solution of 10.0 g. of 6-(2-naphthyloxy)-1-hexanol O-methanesulfonate and 9.7 g. of ethyl 4-aminobenzoate in 50 ml. of hexamethylphosphoramide is heated at 110° C. for 16 hours. The solution is cooled, diluted with water, filtered and the solid washed with ethanol and water to give 7.7 g. of product. Recrystallization from ethanol and once from acetone-hexane gives crystals, m.p. 109°–110° C.

EXAMPLE 4 p-{[6-(2-Naphthyloxy)hexyl]amino}benzoic acid

A solution of 4.8 g. of ethyl p-{[6-(2-naphthyloxy)hexyl]amino}benzoate and 4.8 g. of potassium hydroxide in 100 ml. of 95% ethanol is refluxed for 3 hours. The solution is cooled, diluted with water and acidified with concentrated hydrochloric acid. The mixture is filtered and the solid washed with ethanol and water and recrystallized from ether-methylene chloride and acetone to give crystals, m.p. 157°–159° C.

EXAMPLE 5

2-(2-Naphthyloxy)ethanol

A solution of 14.4 g. of 2-naphthol, 12.1 g. of 2-bromoethanol and 5.9 g. of sodium methoxide in 100 ml. of ethanol is allowed to stand two days at room temperature. The solvent is removed under vacuum and the residue extracted with ether. The ether extract is washed with water, dried (magnesium sulfate) and the solvent removed under vacuum to give crystals, m.p. 65°–70° C.

EXAMPLE 6

2-(2-Naphthyloxy)ethanol O-methanesulfonate

As described in Example 2, 13.5 g. of 2-(2-naphthyloxy)ethanol in 400 ml. of dichloromethane is reacted with 9.5 g. of methanesulfonyl chloride in the presence of 11.4 g. of triethylamine to give the product as tan crystals.

EXAMPLE 7

Ethyl p-{[2-(2-naphthyloxy)ethyl]amino}benzoate

A mixture of 18.7 g. of 2-(2-naphthyloxy)ethanol O-methanesulfonate and 23.6 g. of ethyl p-aminobenzoate is heated in 300 ml. of hexamethylphosphoramide at 110° C. for 16 hours. The mixture is cooled, diluted with water and worked up as described in Example 3 to give the crystalline product. Recrystallization from ethanol gives crystals, m.p. 158°–162° C.

EXAMPLE 8

2-(1-Naphthyloxy)ethanol O-methanesulfonate

To a solution of 18.8 g. of 2-(1-naphthyloxy)ethanol and 15.1 g. of triethylamine in 425 ml. of dichloromethane is added 12.6 g. of methanesulfonyl chloride as described in Example 2 to give the product.

EXAMPLE 9

Ethyl p-{[2-(1-naphthyloxy)ethyl]amino}benzoate

A solution of 29.1 g. of 2-(1-naphthyloxy)ethanol O-methanesulfonate and 33 g. of ethyl p-aminobenzoate in 100 ml. of hexamethylphosphoramide is heated at 100° C. for 16 hours. The solution is worked up as described in Example 3 to give the product. Recrystallization gives crystals, m.p. 124°–127° C.

EXAMPLE 10 p-{[2-(1-Naphthyloxy)ethyl]amino}benzoic acid

A solution of 12 g. of ethyl p-[2-(1-naphthyloxy)ethylamino]benzoate and 15.8 g. of potassium hydroxide in 100 ml. of 95% ethanol is refluxed for 3 hours. The solution is diluted with 75 ml. of water and acidified with concentrated hydrochloric acid. The solid is filtered, washed with 50% ethanol and with water. Recrystallization from ethanol gives the product as crystals, m.p. 193°–194° C.

EXAMPLE 11 p-{[2-(2-Naphthyloxy)ethyl]amino}benzoic acid

A mixture of 3.0 g. of ethyl p-{[2-(2-naphthyloxy)ethyl]amino}benzoate, and 3.0 g. of potassium hydroxide in 200 ml. of ethanol-water (95:5) is refluxed for 3 hours. The mixture is diluted with 100 ml. of water and brought to pH 6.0 with concentrated hydrochloric acid. The mixture is filtered and the solid washed with 50 ml. of water and 20 ml. of cold ethanol-water (4:1) to give the product, m.p. 208°–211° C.

EXAMPLE 12

Enhancement of glucose oxidation

The enhancement of glucose oxidation by insulin was measured using fat cells isolated from the rat. These adipocytes were obtained by collagenase digestion of rat epididymal fat pads. The cells were then incubated at 37° C. for one hour in bicarbonate buffer (3% albumin) containing 0.3 mM glucose-U-$^{14}$C and insulin in the absence and in the presence of 100 mcg/ml of the compound being tested. At the end of the incubation period, $^{14}CO_2$ was collected in Hyamine Hydroxide ® (New England Nuclear) and the radioactivity counted by liquid scintillation spectrometry. The effect of the compound in increasing the sensitivity of the cells to insulin was calculated from the ratio of the action of insulin on glucose oxidation in the presence and absence of the test compounds, expressed as percent enhancement of the insulin effect.

TABLE II

| Compound of Example No. | % Enhancement of Insulin Action |
|---|---|
| 10 | 61% |
| 15 | 71% |
| 30 | 50% |
| 32 | 37% |
| 35 | 51% |

EXAMPLE 13

Hypoglycemic effect on diabetic mice

The hypoglycemic effect of such compounds on diabetic mice is demonstrated by the following example. Obese mice with diabetes were caged individually and allowed to eat ad libitum ground chow, with or without the compound under test. The compound was uniformly applied as a solution in methanol to the food which was blended by tumbling and then dried to remove the methanol. A control group of 8 mice was given normal food while another group of 8 was given the same food containing a weighed amount of antidiabetic compound. The dosage of compound can be determined from the amount of food consumed. At the end of the 5-day or 24-day experiment, blood samples were taken from each animal. The serum-glucose concentrations were measured in a Beckman Glucose Autoanalyzer.

TABLE III

| p-{[2-(1-naphthyloxy)ethyl]-amino}benzoic acid of Example 10 | | | |
|---|---|---|---|
| % in food | mg/kg orally | Serum Glucose mg/dl | Duration of Experiment |
| 0.23% | | 153 | 5 days |
| 0 (controls) | | 340 | |
| 0.03% | | 334 | 5 days |
| 0 (controls) | | 412 | |
| 0.23% | | 158 | 24 days |
| 0 (controls) | | 287 | |
| 0.1% | | 143 | 24 days |
| 0 (controls) | | 287 | |
| | 200 | 192 | 1 hour |
| | 0 | 249 | |

EXAMPLE 14

Ethyl p-{[2-(4-chloro-1-naphthyloxy)propyl]amino}benzoate

To a cold, stirred solution of ethyl p-[2-(4-chloro-1-naphthyloxy)propionamido]benzoate (9.5 g.) in 100 ml. dry tetrahydrofuran is added slowly 35 ml. of 1 M diborane in tetrahydrofuran. The reaction mixture is stirred at room temperature for 20 minutes, then refluxed for 3½ hours. The mixture is poured onto 500 ml. of ice, giving a cloudy solution. After saturating this solution with sodium chloride, it is extracted twice with ether and twice with chloroform. The combined organic phases are dried and flash-evaporated to a yellow oil. The oil is dissolved in a small amount of ethyl acetate and hexane and purified on a column of silica gel, giving a white powder, m.p. 122° C.

EXAMPLE 15 p-{[2-(4-Chloro-1-naphthyloxy)propyl]amino}benzoic acid

To the ester (3.0 g.) of the previous example in 40 ml. of 95% ethanol is added potassium hydroxide (0.57 g., 85% KOH) with stirring. After refluxing 4 hours, the solution is cooled, diluted with 60 ml. of water and acidified to pH 3 with concentrated HCl. The precipitate is collected, washed with water, dried in vacuo and recrystallized from acetonitrile-water to give crystalline material, m.p. 165°–168° C.

EXAMPLE 16

Ethyl 4-[2-(α-naphthyloxy)propylamino]benzoate

A solution of 8.29 g. ethyl 4-[2-(1-naphthyloxy)propionamido]benzoate in 75 ml. tetrahydrofuran is reacted with 34 ml. 1 M diborane in tetrahydrofuran. After stirring at room temperature for 5 days, the solution is poured into 750 ml. 5% HCl, stirred for about ½ hour until foaming stopped, and extracted three times with 250 ml. portions of methylene chloride. The combined extracts are washed with 200 ml. brine, dried and condensed to nearly colorless oil. Crystallization from acetonitrile yield white solid, m.p. 110°–111.5° C.

EXAMPLE 17

4-[2-(α-Naphthyloxy)propylamino]benzoic acid

A solution of 4.21 g. of the ester of the previous example and 2.4 g. of 85% KOH in 75 ml. 95% ethanol is stirred at 80° for 5 hours. After the cooled solution is evaporated, the residue is dissolved in 100 ml. $H_2O$, adjusted to pH 4 with 37% HCl and extracted twice with 100 ml. portions of methylene chloride. The solid from evaporation of the solvent is crystallized from toluene to yield tan crystals, m.p. 142°–144° C.

EXAMPLE 18

3-[2-(1-Naphthyloxy)ethylamino]benzoic acid

A solution of 3.2 g. of methyl 3-[2-(1-naphthyloxy)ethylamino]benzoate and 1.68 g. of potassium hydroxide in 40 ml. of 95% ethanol is heated to reflux for 4 hours. After cooling and diluting with 80 ml. of water, the solution is acidified with concentrated HCl and filtered. Recrystallization from acetonitrile affords the white desired product, m.p. 150°–152° C.

EXAMPLE 19

3-[2-(1-Naphthyloxy)ethylamino]benzoate

A solution of 5.8 g. of 2-(1-naphthyloxy)ethyl bromide and 6.95 g. of methyl m-aminobenzoate in 40 ml. of hexamethylphosphoramide is stirred at 65° for 16 hours. After cooling and diluting with 80 ml. of water, the mixture is extracted twice with ether. The combined ether extracts are washed with dilute acid, then with water, dried and then evaporated to an orange solid. Recrystallization from ethanol and then from acetonitrile affords white material, m.p. 113.5°–115° C.

EXAMPLE 20

4-[3-(α-Naphthyloxy)propyl]aminobenzoic acid

A solution of 6 g. of ethyl 4-[3-(1-naphthyloxy)propylamino]benzoate and 3.4 g. of 85% KOH in 75 ml. 95% ethanol is heated at 80° C. for 4 hours, the reaction then diluted with 150 ml. of water and adjusted to pH 3 with 37% HCl. The resulting oily solid is extracted using several portions of warm ether. The extracts are combined, dried, and evaporated to a solid which is crystallized from acetonitrile to yield crystals, m.p. 146°–147° C.

EXAMPLE 21

Ethyl 4-[3-(α-naphthyloxy)propyl]aminobenzoate

A solution of 10 g. 3-(α-naphthyloxy)propyl bromide and 12.5 g. ethyl 4-aminobenzoate in 100 ml. hexamethylphosphoramide is stirred at 110° for 15 hours. The cooled solution is diluted with 200 ml. water and extracted 3 times with 100 ml. portions of ether. The combined extracts are washed with brine, dried and evaporated to an orange residue. The product is crystallized from ethanol to yield a solid which is crystallized from ethanol to yield white crystals, m.p. 93°–94° C.

EXAMPLE 22

Ethyl p-{[1-methyl-2-(1-naphthyloxy)ethyl]amino}benzoate

A mixture of 1.26 g. of 57% sodium hydride-in-oil (previously washed with petroleum ethers) in 60 ml. of HMPA with 4.33 g. of 1-naphthol is stirred for one hour. To this is added 6.15 g. of 2-methyl-1-(4-carboethoxyphenyl)aziridine followed by heating at 100° for 18 hours. After cooling and diluting with 120 ml. of water, product is extracted with ether and the combined extracts are washed with water, dried and evaporated to a yellow oil. Trituration with ethanol affords a white solid, m.p. 123°–125° C.

EXAMPLE 23 p-{[1-Methyl-2-(1-naphthyloxy)ethyl]amino}benzoic acid

A solution of 1.95 g. of the ester of the previous example and 0.94 g. of potassium hydroxide in 20 ml. of 95% ethanol is heated to reflux for 4 hours. After cooling and diluting with 40 ml. of water and acidification with concentrated HCl, the resulting white solid is recrystallized from ethanol, m.p. 194°–197° C.

EXAMPLE 24

4-{[2-(4-Cyano-1-naphthyloxy)ethyl]amino}benzoic acid

A solution of 4.3 g. of ethyl 4-[N-trifluoroacetyl-2-(4-cyano-1-naphthyloxy)ethylamino]benzoate and 4.3 g. of potassium hydroxide in 100 ml. of 95% ethanol is refluxed for 3 hours. After cooling, diluting with 100 ml. of water and acidification to pH 4 with concentrated hydrochloric acid, the white solid is collected, washed with water and dried, m.p. 254°–256° C.

EXAMPLE 25

Ethyl 4-[N-trifluoroacetyl-2-(4-cyano-1-naphthyloxy)ethylamino]benzoate

To a solution of 5.4 g. of ethyl 4-[N-trifluoroacetyl-2-(1-naphthyloxy)ethylamino]benzoate and 1.5 g. of cyanogen bromide in 200 ml. of methylene chloride at −5° C. is added 5.7 g. of anhydrous aluminum chloride. The solution is allowed to stand at room temperature for 5 hours and then poured into 200 ml. of ice and water. After addition of 20 ml. of concentrated hydrochloric acid, the organic layer is seperated, washed with water, dried and evaporated to dryness. Recrystallization from 75% aqueous acetonitrile gives material, m.p. 150°–151° C.

EXAMPLE 26

4-[2-(4-Acetyl-1-naphthyloxy)ethylamino]benzoic acid

By the procudure of Example 24, this acid is prepared from the analogous 4-acetyl compound from Example 27. The crystals melted at 276°–278° C.

EXAMPLE 27

Ethyl 4-[N-trifluoroacetyl-2-(4-acetyl-1-naphthyloxy)ethylamino]benzoate

To a solution of 5.4 g. of ethyl 4-[N-trifluoroacetyl-2-(1-naphthyloxy)ethylamino]benzoate and 5.7 g. of anhydrous aluminum chloride at 0° C. is added 1.1 g. of acetyl chloride with stirring. After 1 hour at 0° C., the solution is poured over 200 g. of ice plus 20 ml. concentrated hydrochloric acid. The organic phase is separated and the aqueous phase re-extracted. After washing with dilute acid, the methylene chloride extract is evaporated to dryness. The residue is crystallized from acetonitrile, m.p. 160°–161° C.

EXAMPLE 28

Sodium 4-[2-(1-naphthyloxy)ethylamino]benzoate

To a solution of 1.42 g. sodium methoxide in 250 ml. methanol is added 8.0 g. of 4-[2-(1-naphthyloxy)ethylamino]benzoic acid. After one-half hour, the mixture is concentrated under vacuum to a solid which is washed with methanol and then $CH_2Cl_2$. This solid is immediately dried in a vacuum oven to minimize absorption of moisture from the air.

EXAMPLE 29

Ethyl 4-[2-(1,2,3,4-tetrahydro-5-naphthyloxy)ethylamino]benzoate

To a slurry of 2.3 g. of 57% sodium hydride-in-oil (previously washed free of oil with hexane) in 20 ml. of dimethoxyethane is added 7.4 g. of 1,2,3,4-tetrahydro-5-naphthol in 20 ml. of dimethoxyethane and then 13.6 g. of ethyl 4-(2-bromoethylamino)benzoate. After refluxing for 6 hours and dilution with 300 ml. of water, the solid is collected and recrystallized from acetonitrile, m.p. 133°–135° C.

EXAMPLE 30

4-[2-(1,2,3,4-Tetrahydro-5-naphthyloxy)ethylamino]benzoic acid

Using the procedure of Example 20 on the ester of Example 29, this acid is prepared with m.p. 216°–218° C.

EXAMPLE 31

Ethyl 2-{[2-(1-naphthyloxy)ethyl]amino}benzoate

A solution of 12.54 g. of 2-(1-naphthyloxy)ethyl bromide and 16.5 g. of ethyl anthranilate in 50 ml. of hexamethylphosphoramide are heated at 110° for 18 hours. After cooling and diluting with water, the mixture is extracted twice with 200 ml. of ether. The combined ether extracts are washed with water, dried and evaporated to a brown oil. The oil is dissolved in 60 ml. of ethanol and chilled in an ice-bath yielding a beige solid which is recrystallized from 100 ml. of ethanol affording pale yellow crystals, m.p. 81°–83° C.

EXAMPLE 32

2-{[2-(1-Naphthyloxy)ethyl]amino}benzoic acid

Using the procedure of Example 20 on the ester of Example 31, this acid is obtained with m.p. 170°–172° C.

EXAMPLE 33

4-[N-Trifluoroacetyl-2-(1-naphthyloxy)ethylamino]benzoic acid

To 14 ml. of trifluoroacetic anhydride in 25 ml. of tetrahydrofuran is added 4-[2-(1-naphthyloxy)ethylamino]benzoic acid. After one hour, the solution is poured into ice water and the mixture is extracted twice with 100 ml. methylene chloride. The extract is dried and evaporated to dryness. The residue is chromatographed on silica with ether and ethyl acetate. The material isolated melts at 167°–168° C.

EXAMPLE 34

Ethyl p-{[2-(4-bromo-1-naphthyloxy)ethyl]amino}benzoate

The solution of 7.0 g. of 2-(4-bromo-1-naphthyloxy)ethyl bromide and 7.9 g. of ethyl 4-aminobenzoate in 50 ml. of hexamethylphosphoramide is heated for 18 hours, then cooled and diluted with 50 ml. of water. The precipitate is collected and crystallized from 200 ml. of methylcyclohexane and then from 100 ml. of ethanol, m.p. 126°–127° C.

EXAMPLE 35

4-[2-(4-Bromo-1-naphthyloxy)ethylamino]benzoic acid

Using the procedure of Example 20 on the ester of Example 34, this acid is obtained with m.p. 247°–248° C. after recrystallization from 1:1 tetrahydrofuran-hexane.

EXAMPLE 36

4-[N-Acetyl-2-(1-naphthyloxy)ethylamino]benzoic acid

A solution of 6.14 g. of 4-[2-(1-naphthyloxy)ethylamino]benzoic acid and 20 ml. of acetyl chloride in 50 ml. pyridine is warmed on a steam-bath for 8 hours. The dark solution is then poured into 370 ml. of 2 N hydrochloric acid. The resulting solution is then extracted several times with methylene chloride. The residue from evaporation of this extract is crystallized from acetonitrile giving a white solid, m.p. 182°–183° C.

EXAMPLE 37

4-[N-Ethyl-2-(1-naphthyloxy)ethylamino]benzoic acid

To a solution of 19.8 g. of acetic acid in tetrahydrofuran at 25° C. is added 3.79 g. of sodium borohydride in portions with cooling. The slurry is allowed to evolve hydrogen over 2 hours at room temperature. A solution of 6.14 g. of 4-[2-(1-naphthyloxy)ethylamino]benzoic acid in 50 ml. of tetrahydrofuran is then added and the mixture brought to reflux. After 18 hours the reaction mixture is cooled and poured into 200 ml. of ice and water. After acidification and fractional extraction with methylene chloride, the white solid obtained by evaporation is crystallized from acetonitrile, m.p. 205°–206° C.

We claim:

1. A compound of the formula:

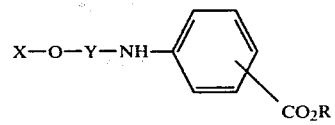

wherein Y is a straight-chain or branched alkylene group of the formula $C_nH_{2n}$ wherein n is an integer from 2 to 12, inclusive; R is hydrogen, lower alkyl, phenyl, p-chlorophenyl, benzyl, lower alkoxyethyl, 3-(lower alkoxy)-2-hydroxypropyl, 2,3-dihydroxypropyl, 3-(lower alkanoyl)oxy-2-hydroxypropyl or pyridylmethyl; and X is naphthyl, 1,2,3,4-tetrahydronaphthyl or naphthyl substituted with halo, cyano, carbamoyl, carboxy, lower alkanoyl, lower alkoxy, lower alkanoylamino, lower alkanosulfonamido or sulfamyl; the pharmacologically acceptable acid-addition salts thereof; and the pharmacologically acceptable cationic salts thereof.

2. A compound of the formula:

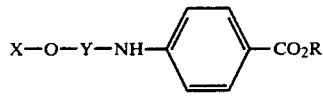

wherein Y is a straight-chain or branched alkylene group of the formula $C_nH_{2n}$ wherein n is an integer from 2 to 12, inclusive; R is hydrogen alkyl having up to 6 carbon atoms; and X is naphthyl, 1,2,3,4-tetrahydronaphthyl 4-chloro-1-naphthyl, the pharmacologically acceptable acid-addition salts thereof; and the pharmacologically acceptable cationic salts thereof.

3. A compound according to claim 2 wherein Y is a straight-chain or branched alkylene group of the formula $C_nH_{2n}$ wherein n is an integer from 2 to 6, inclusive.

4. The compound according to claim 2 wherein Y is ethylene, R is hydrogen and X is 1-naphthyl; p-{[2-(1-naphthyloxy)ethyl]amino}benzoic acid.

5. The compound according to claim 2 wherein Y is ethylene, R is hydrogen and X is 4-chloro-1-naphthyl; p-{[2-(4-chloro-1-naphthyloxy)ethyl]amino}benzoic acid.

6. The compound according to claim 2 wherein Y is 2-propylene, R is hydrogen and X is 4-chloro-1-naphthyl; p-{[2-(4-chloro-1-naphthyloxy)propyl]amino}benzoic acid.

7. The compound according to claim 2 wherein Y is ethylene, R is hydrogen and X is 4-bromo-1-naphthyl; p-{[2-(4-bromo-1-naphthyloxy)ethyl]amino}benzoic acid.

8. The compound according to claim 1 wherein Y is ethylene, R is hydrogen and X is 1-naphthyl; o-{[2-(1-naphthyloxy)ethyl]amino}benzoic acid.

9. The compound according to claim 2 wherein Y is 2-propylene, R is hydrogen and X is 1-naphthyl; p-{[2-(1-naphthyloxy)propyl]amino}benzoic acid.

10. The compound according to claim 2 wherein Y is ethylene, R is hydrogen and X is 1,2,3,4-tetrahydro-5-naphthyl; p-{[2-(1,2,3,4-tetrahydro-5-naphthyloxy)ethyl]amino}benzoic acid.

* * * * *